Figure 1:
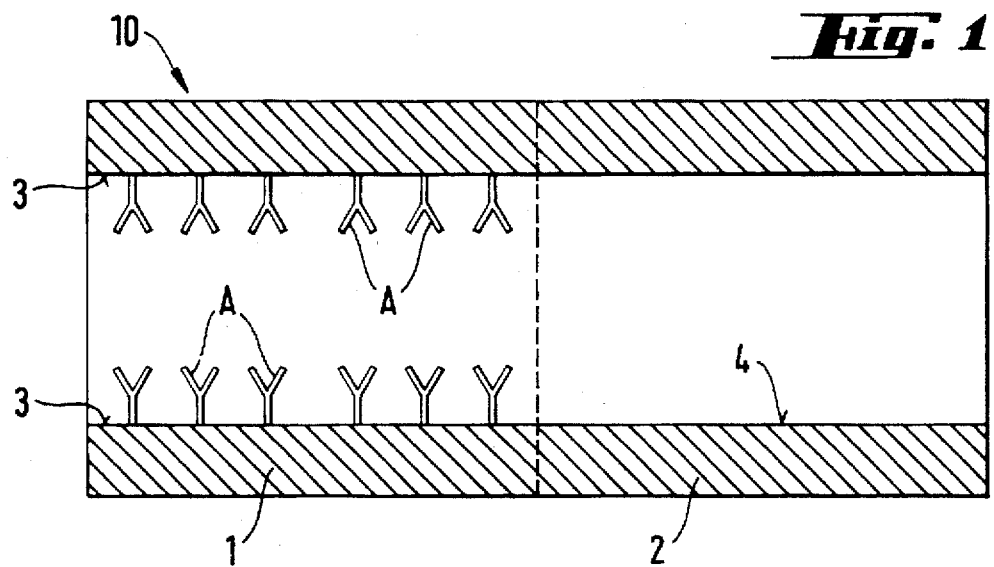

United States Patent [19]
Ensing et al.

[11] Patent Number: 5,741,639
[45] Date of Patent: Apr. 21, 1998

[54] DEVICE AND METHOD FOR COMBINED BIOAFFINITY ASSAY AND ELECTROPHORETIC SEPARATION OF MULTIPLE ANALYTES

[75] Inventors: Kees Ensing, Roodeschool, Netherlands; Peter Oroszlan, Basel, Switzerland; Aran Paulus, Heitersheim; Carlo S. Effenhauser, Weil am Rhein, both of Germany

[73] Assignee: Ciba-Geigy Corp., Summit, N.J.

[21] Appl. No.: 396,310

[22] Filed: Feb. 28, 1995

[30] Foreign Application Priority Data

Mar. 8, 1994 [DE] Germany ............... 94 810 146.4

[51] Int. Cl.$^6$ ............................................. C12Q 1/68
[52] U.S. Cl. ..................... 435/6; 435/7.1; 435/960; 435/961; 436/541; 436/810; 422/70; 422/101; 422/807; 422/810; 204/452; 204/455
[58] Field of Search ............... 422/70, 810, 82.02, 422/82.03, 99, 514, 101, 807; 435/7.1, 287.1-2, 7.93, 7.94, 9.95, 960, 961, 288.1, 516, 288.5; 436/518, 810, 527, 535, 538, 541; 204/164, 180.1, 182.8, 183.2, 183.3, 451-2, 455; 424/57, 58

[56] References Cited

U.S. PATENT DOCUMENTS

| | | | |
|---|---|---|---|
| 4,865,707 | 9/1989 | Karger et al. | 204/182.8 |
| 5,013,669 | 5/1991 | Peters, Jr. et al. | 436/518 |
| 5,135,627 | 8/1992 | Soane | 204/182.8 |

FOREIGN PATENT DOCUMENTS

| | | | |
|---|---|---|---|
| 2498331 | 7/1982 | France | G01N 31/32 |
| 8202211 | 7/1982 | WIPO | C12M 1/40 |

OTHER PUBLICATIONS

Effenhauser et al. Glass Chips for High-Speed Capillary Electrophoresis Sepa. W/Submicro. Plate heights, 1993, 2637.
Effenhauser et al. High-Speed. Sep. of Antisense Oligo. on a Micromachined Cap. electr. device, 1994,2949.
Chen et al., Semi-automa., Jour.Chro. 1993, 289–294.
Derw. Abst. 93–253558 of JP 5172815

Primary Examiner—Christopher L. Chin
Assistant Examiner—Bao-Thuy L. Nguyen
Attorney, Agent, or Firm—George R. Dohmann

[57] ABSTRACT

A device for combined bioaffinity assay and electrophoretic separation is provided, which comprises a capillary system having two stages, a first stage in which bioaffinity interactions of analyte molecules and molecular recognition elements are performed, and a second stage, in which electrophoretic separation of the analyte molecules and subsequent detection of the separated species is accomplished. Within the first capillary stage the molecular recognition elements are attached and immobilized to the inside capillary wall, for example, by adsorption or by covalent binding to the capillary material. The method for combined bioaffinity assay and electrophoretic separation comprises flowing an analyte through a capillary system having two stages. In a first capillary stage the analyte molecules are captured by respective molecular recognition elements present in that stage. More particularly the analyte molecules are captured by molecular recognition elements which are attached and immobilized to the inside wall of that capillary stage, for example, by adsorption or by covalent binding to the capillary material. After a predetermined time the analyte-molecules are dissociated from the molecular recognition elements. Subsequently the analyte-molecules are separated in a second stage of the capillary system by capillary electrophoresis and finally the separated species are detected at the terminal part of the capillary system.

16 Claims, 2 Drawing Sheets

DEVICE AND METHOD FOR COMBINED BIOAFFINITY ASSAY AND ELECTROPHORETIC SEPARATION OF MULTIPLE ANALYTES

The invention concerns a device for combined bioaffinity assay and electrophoretic separation according to the preamble of patent claim 1. The invention also concerns a method for accomplishing a combined bioaffinity assay and electrophoretic separation according to the preamble of patent claim 14.

In the past bioaffinity assays and more specifically immunochemical methods have been mainly used for qualitative and quantitative analysis of drugs and hormones present in biological matrices in low concentrations. Clean-up steps are often not required, because most endogenous compounds do not directly or indirectly interfere with the specific antigen-antibody binding. An important side effect of the selective, bioaffinity extraction of analytes from a biological matrix is that at the same time substantial concentration of analytes is obtained. An antibody only recognizes a small part of the antigen-molecule, the so-called epitope. Any molecule containing such an epitope accessible for the antibody, will bind as if it were the analyte of interest. The impact is largely dependent on the relative affinity to the antibody and the relative concentration of the antibody molecule in comparison with the affinity and concentration of the analyte. The cross-reactivity in antigen-antibody binding of structural analogues can not always be controlled in a manner that only a single analyte will interact with the antibody. A positive effect of cross-reactivity of molecular recognition elements is that they are nowadays often employed for the preconcentration of analytes either off-line or on-line with chromatographic and/or spectroscopic analytical procedures.

There have been attempts for a combination of immuno affinity and capillary electrophoresis (CE) hoping to achieve a different type of selectivity in comparison to immuno affinity chromatography. The resolving power of CE is large in comparison with liquid chromatography while the utilisation of other physico-chemical properties for the separation can in many cases contribute to an increase of the selectivity of the analytical system.

In a known attempt to use bioaffinity assay (BA), or, more specifically, immuno assay preconcentration in combination with CE antibodies were immobilized on the surface of aminopropyltriethoxysilyl derivatized glass beads. After modification of the surface of the glass-beads with 1,4-phenylene diisothiocyanate monoclonal antibodies were coupled thereto. The glass-beads were filled into a capillary between two glass frits. Filling the coated glass beads into the capillary is usually performed by hand. This procedure is rather difficult to achieve and, moreover, is very labor-intensive. One major drawback of filling capillaries with glass beads is, that the chance of blocking the capillary is dramatically increased. Also, the binding of the analyte molecules to the antibodies is not uniform, due to the unpredictable and inhomogeneous flow conditions in the glass beads filled capillary. Thus, dependent on the location of the glass beads within the capillary the association and dissociation kinetics is different. Differences in mass-transport of the analyte molecules from the solution to the antibodies, however, can give rise to peak broadening, which results in a reduction of the resolution of the device.

While the state of the art is explained by way of example of an antigene-antibody interaction with subsequent capillary electrophoresis, it is to be understood that these above identified disadvantages apply to all comparable attempts of a general analyte molecule-molecular recognition element interaction. Such general interactions are, for example, antibody-antigen complexation, receptor-drug interactions, specific protein-protein interactions, DNA-protein interactions, DNA-hybridization assays and still further comparable interactions. It is therefore an object of the present invention to provide a device and a method for combined bioaffinity assay and capillary electrophoresis, which combines the advantages of each single concept and overcomes the disadvantages of the known attempts. The chance of blocking the capillaries shall be avoided. The flow conditions for the analyte within the capillaries shall be predictable and generally homogeneous. Location-dependent effects of the association and dissociation kinetics of the analyte molecule-molecular recognition element interaction shall be avoided such, that a high separation efficiency can be achieved.

All these and still further objects are resolved by a device and a method for combined bioaffinity assay and electrophoretic separation which comprise the features listed in the characterizing parts of the respective independent patent claims. More specifically, according to patent claim 1 a device for combined bioaffinity assay and electrophoretic separation is provided, which comprises a capillary system having two stages, a first stage in which bioaffinity assay interaction of analyte molecules and molecular recognition elements is performed and a second stage, in which electrophoretic separation of the analyte molecules and subsequent detection of the separated species is accomplished. Within the first capillary stage the molecular recognition elements are attached and immobilized to the inside capillary wall, for example, by adsorption or by covalent binding to the capillary material. By having the molecular recognition elements attached and immobilized directly to the inside wall of the capillary, obstacles within the flowing path of the analyte am avoided. Therefore, the danger of blocking the capillary tube is practically removed. The flow conditions are predictable and depend mainly only on the flow velocity of the analyte within the capillary tube. Location-dependent effects of the association and dissociation kinetics of the analyte molecule molecular recognition element interaction are avoided. The molecular recognition elements which are attached and immobilized to the capillary inside wall are, for example, antibodies, antigens, receptors, drugs, DNA-strands, carbohydrates, and similar recognition elements, or combinations of two or more of these elements. The attachment and immobilization of the molecular recognition elements to the inside capillary wall can easily be performed automatically such, that manual labor is reduced. In addition this automatization results in a high precision of the device, which thus can be identically mass-produced.

In a preferred embodiment of the invention the capillary system is established preferably planarely on a small slab of glass, polymer, or semiconducting material by micromachining or by standard techniques known from microelectronics industry. This specific embodiment of the invention has the advantage, that, if desired, even electric couplings for electrodes for establishing an electric field and for detecting signals from a detector for electrophoretically separated species can be integrated on the slab of glass, polymer, or semiconducting material. The molecular recognition elements are attached to the inside walls of the first stage of the capillary system. In order to provide a sufficiently large surface for attaching the molecular recognition elements, the total length of first stage of the capillary system can be enlarged in a controlled manner, for example, by providing a controlled roughness of the side walls, or by providing a meander-shaped channel. Thus, unlike to the situation in which the molecular recognition elements, i.e. the antibodies, are attached to the surface of glassbeads that are randomly distributed within a capillary, the flow conditions are controllable and predictable. The overall dimensions of this chip-embodiment of the invention am very small; such chip-solutions at the most have the size of a conventional semiconductor wafer, and usually they are considerably smaller such, that a number of chips can be established simultaneously on one wafer. This particularly contributes to an easy and cheap manufacture of the device according to the invention.

The method for combined bioaffinity assay and electrophoretic separation according to independent claim 14 comprises flowing an analyte through a capillary system having two stages. In the first capillary stage the analyte molecules are captured by respective molecular recognition elements present in that stage. More particularly the analyte molecules are captured by molecular recognition elements which are attached and immobilized to the inside wall of that capillary stage, for example, by adsorption or by covalent binding to the capillary material. After a predetermined time the analyte-molecules are dissociated from the molecular recognition elements. Subsequently the analyte-molecules are separated in a second stage of the capillary system by electrophoresis and finally the separated species are detected at the terminal part of the capillary system.

Further preferred embodiments of the device and the method according to the invention are subject of the respective dependent claims. The invention will be explained in more detail in the following description of preferred embodiments with reference to the accompanying drawings. In the drawings FIG. 1 is a schematic representation of a device for combined bioaffinity assay and electrophoretic separation, and FIGS. 2–6 illustrate schematically the method for combined bioaffinity assay and electrophoretic separation.

An exemplary embodiment of the device according to the invention is depicted schematically in FIG. 1 and is generally designated with the reference number 10. It comprises a capillary system of a length from about 0.1 cm to about 200 cm, preferably about 1 cm to about 50 cm and an internal cross-sectional area from about 5 $\mu m^2$ to about 10000 $\mu m^2$. The shape of the internal cross-section of the capillary system can be about circular, rectangular, trapezoidal, or similar. The capillary system also comprises entrance and exit openings for the introduction and the removal of an analyte and a carrier medium (if required). For reasons of simplification of the schematic drawing the respective entrance and exit openings are not depicted in FIG. 1.

The capillary system comprises a first stage 1, in which bioaffinity interaction and preconcentration of analyte molecules are performed and a second stage 2, in which electrophoretic separation of the preconcentrated analyte molecules and subsequent detection of the separated species is accomplished. The electrodes for building up an electric field along the longitudinal extension of the second stage of the capillary system are not depicted in order to simplify the drawing. However, one of ordinary skill in the art will be aware of various embodiments for such electrodes, such as, for example, thin metal rings on the inside wall 4 of the capillary tube which are connected with a thin wire that extends through the capillary wall and ends in an electric coupling provided on the outside of the capillary tube. In a preferred embodiment the capillary system is realized on a small slab of glass or semiconducting material. In that case the electrodes and the couplings could be integrated on the "chip" applying well known manufacture techniques from microchip industry.

In accordance with the invention in the first capillary stage 1 molecular recognition elements A are attached and immobilized to the inside of the capillary wall 3. The molecular recognition elements can be attached to the capillary wall, for example, by adsorption or by covalent binding. However other physical and/or chemical techniques are equally applicable. Adsorptive binding is generally easier to achieve and theoretically opens possibilities for the regeneration of the bioaffinity part of the first stage 1 of the capillary system.

In case that the capillary system is made up of one capillary tube only, the first capillary stage 1 should occupy only a limited length of the capillary. Thus, only a limited length of the capillary should be occupied by molecular recognition elements A, so that a sufficient length of the capillary is available for the actual electrophoretic separation of the analyte molecules after release from the molecular recognition elements A. By a variation of the length of the first stage the mount of molecular recognition elements, which are attached and immobilized to the capillary wall, can be easily controlled and thus the sensitivity of the device can be adapted to the requirements. Preferably the length of the first stage 1 amounts to about 1% to about 95%, preferably less than 25% of the total length of the capillary system. In FIG. 1 and in the subsequent FIGS. 2–6 the first and the second stage are separated by a dotted line.

In a preferred embodiment the capillary system comprises two capillary tubes 1,2. A fast capillary tube which is coated along its entire length on its inside wall 3 with molecular recognition elements, is coupled with a capillary 2 that enables optimal separation conditions. Thus, the length of each stage is easily controlled and can readily be adapted to the requirements. In case that the capillary system comprises two capillary tubes 1,2 the dotted lines in FIGS. 1–6 stand for the ends of the two capillary tubes along which they are attached with each other, and are preferably glued together.

In FIGS. 2–6 the method for combined bioaffinity assay and electrophoretic separation is illustrated for a single class of molecular recognition elements A and one species of analyte molecules, which consist of unlabeled analyte molecules M and labeled analyte molecules L. The labeling of part of the analyte molecules can be achieved by various methods. For example, luminescent, ultraviolet radiating, radioactive, or electrochemically active substances can be used. The device depicted for the illustration of the method according to the invention corresponds to the one shown in FIG. 1. It can comprise one capillary tube only, or it can comprise two or more capillary tubes, such as, for example, a first tube 1 which is coated along its inside wall 3 with the molecular recognition elements A and a second one 2 for carrying out the separation on the principle of capillary electrophoresis. In the Figures the unlabeled analyte molecules M are symbolyzed by the small rectangles while the L-shaped symbols stand for the labeled analyte molecules L. The molecular recognition elements A are bound to a limited length of the internal capillary wall 3 at the injection side of the capillary.

Figure 2:
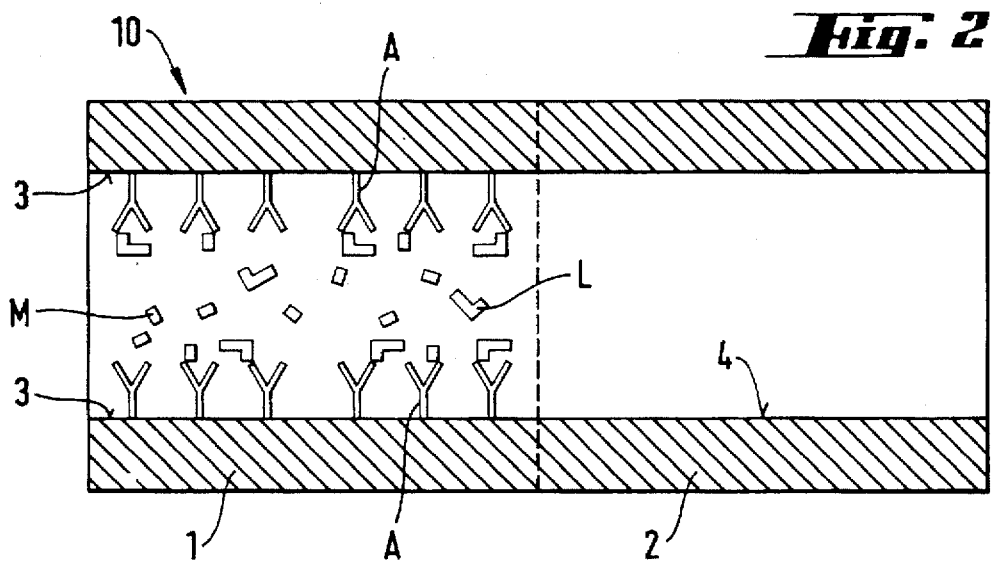

In FIG. 2 a mixture of the unlabeled and labeled analyte molecules M and L of defined concentrations is shown injected into the first stage I of the capillary system so, that these can interact with the molecular recognition elements A on the inside walls of the capillary. With increasing concentrations of the unlabeled analyte molecules M, the amount of the labeled analyte molecules L that is captured by the molecular recognition elements A, will decrease. After an adequate incubation time an equilibrium will be found between the bound and free fractions of the labeled analyte molecules L and of the unlabeled analyte molecules M. As long as standardized assay conditions are maintained, even non-equilibrium conditions can be used.

Figure 3:
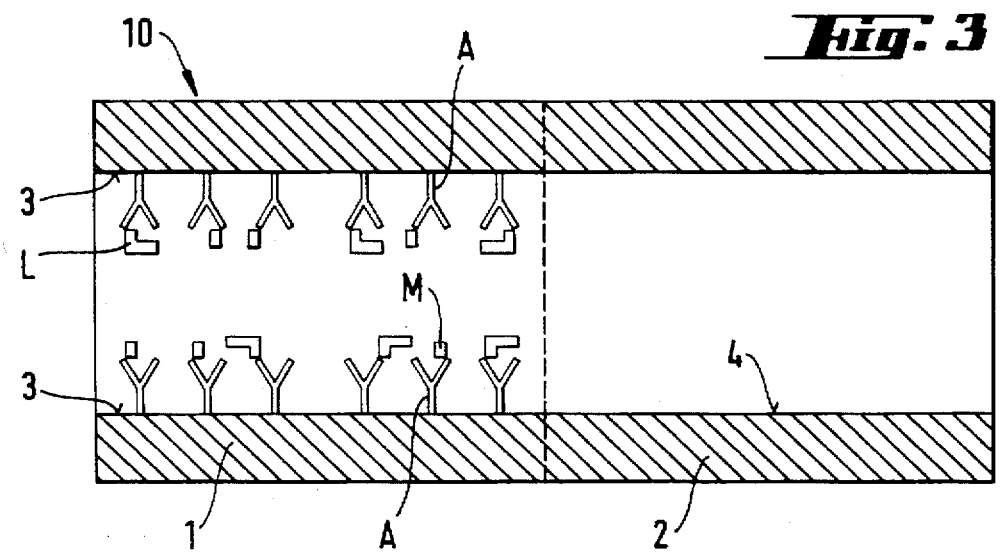

With a rinse procedure, which is indicated in FIG. 3, the unbound fractions of the labeled analyte molecules L and of the unlabeled analyte molecules M are removed from the capillary tube.

Figure 4:
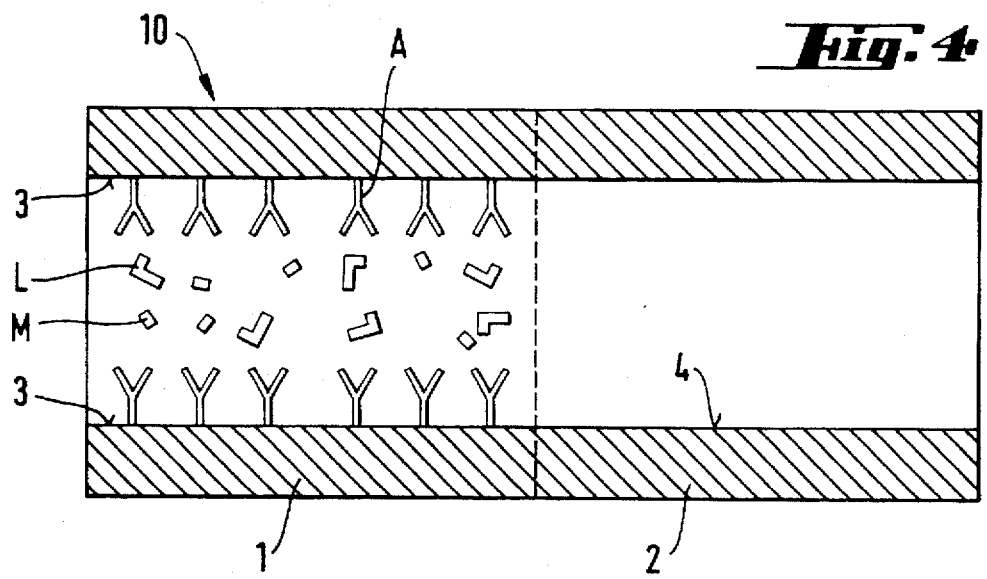

In the next step, which is depicted in FIG. 4, the bound fractions of the labeled and unlabeled analyte molecules L and M are released by the molecular recognition elements A. By injection of a chaotropic agent, e.g. a salt-solution, an organic solvent or another buffer solution, the dissociation-rate can be increased and reassociation can be deminished.

Figure 5:
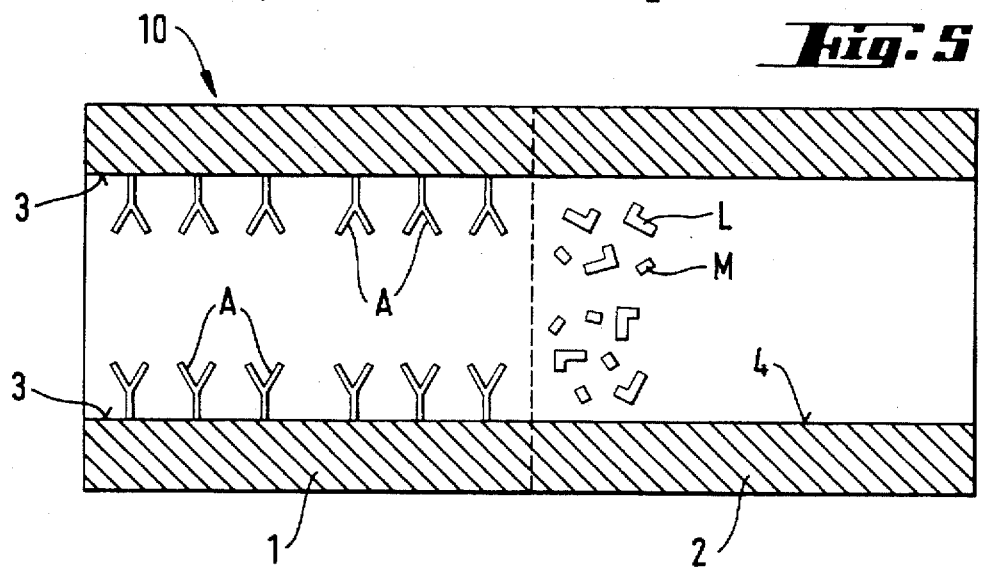

The next step is the separation of the labeled analyte molecules L and the unlabeled analyte molecules M in the electrical field inside the second capillary stage 2. The separation efficiency in capillary electrophoresis CE is, among others, dependent on the size of the injected sample plug. Therefore it is desirable to concentrate the labeled and unlabeled analyte molecules L and M which are spread over the length of the first capillary stage after the dissociation step. This concentration can be achieved by various methods, for example by Isotachophoresis or by isoelectrical focussing. Preferably a field amplified sample concentration is accomplished using the electrical field within the second stage 2. For that purpose the conductivity of the sample with the chaotropic agent and the analyte molecules L and M is chosen smaller than the conductivity of the separation buffer. Then under the condition that the analyte molecules L and M are charged, these are concentrated due to the higher electrical field, as is indicated in FIG. 5.

Figure 6:
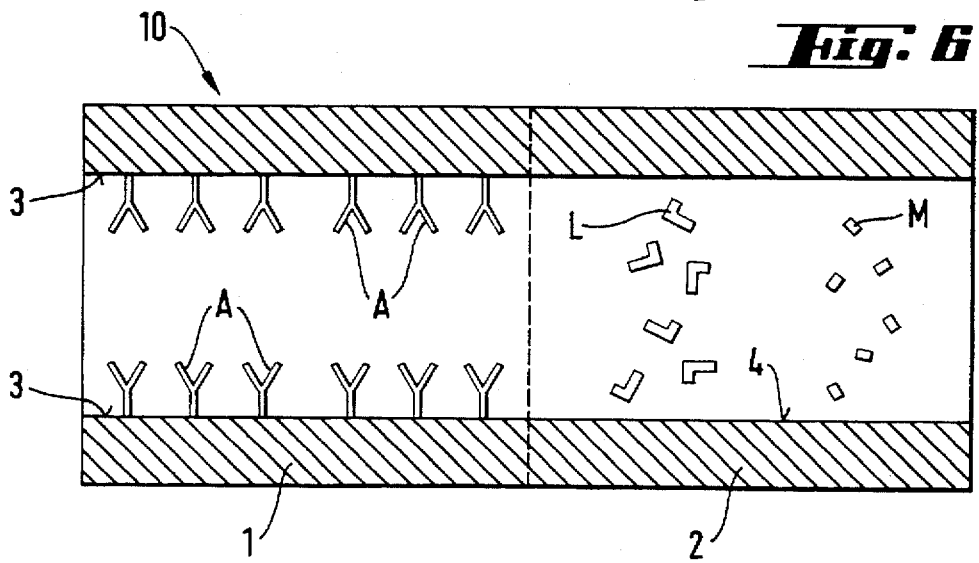

This stacking effect is essential for the efficiency of the separation in the second stage 2 of the capillary system, which is indicated in FIG. 6, and for a precise quantitation of the labeled analyte molecules L. In case the first stage comprises only one type of molecular recognition element A attached to its inside wall, and with one type of labeled analyte molecules L, which can be selectively detected, the separation efficiency does not play a major role. However, for multi-analyte assays employing different molecular recognition elements and labels, it is apparent that the separation efficiency is very important.

For illustrative purposes only an exemplary embodiment of a device according to the invention which is coated along its inside capillary wall of the first stage with antibodies is described hereinafter:

Chemicals

A ready to use 20 mM sodium tetraborate buffer pH=8.0 (BB8) can be obtained from Fluka (Bachs, Switzerland), a ready to use 69 mM sodium-potassium phosphate buffer pH=7.0 (PB7) can be obtained by Ciba-Geigy (Basel, Switzerland), methanol and toluol of chemical grade and milli-Q water should be used. Atrazine, 2-ethylamino-4-chloro-6-isopropylamino-1,3,5-triazine, monoclonal antibodies against atrazine and fluoresceine labeled atrazine (FA) are obtained from internal sources of the applicant. Bovine Serum Albumine (BSA) can be obtained from Fluka (Bachs, Switzerland) and may be used without further purification.

Instrumentation and capillary electrophoresis conditions

A P/ACE 2100 electropherograph equipped with a fluorescence detector or a UV detector is used (Beckman Instruments, Fullerton Calif., USA). A 15 mW Argon laser (Spectra-Physics, Mt. View Calif., USA) operating at 488 nm and a custom-build optical system, delivering 5 mW at the end of the optical fiber positioned on the detection window of the capillary can be used for excitation of the fluoresceine labeled analyte molecules. Electrophoretic separations can be made by applying, for example, 20 to 30 kV over the capillary, which is kept at 30° C., injections usually are made by pressure.

Coating procedures

Coated capillaries are custom made after cleaning fused silica capillaries with 1M KOH for 2 h, rinsing with water for 10 min and rinsing with 0.1M HCl for 10 min and drying for 3 h at 200° C. during which the capillary is flushed with nitrogen. Coating with (mercaptomethyl) dimethylethoxysilane (MDS, Fluka, Buchs Switzerland) can be done by filling the capillary with this reagent and placing it for 18 h in an oven at 200° C. under vacuum in order to obtain a monolayer on the capillary wall.

Coating with 3-aminopropyltrimethoxysilane (Aldrich, Steinhelm, Germany) can be done by filling the capillary with a 2% solution in toluol and heating the capillary at 100° C. for 3 h. After this the capillary is rinsed with methanol for 10 min. This aminopropyl coated capillary can be used for covalent binding of antibodies and BSA after treatment with 0.5% glutaraldehyde (Merck, Darmstadt, Germany) in PB7 for 4 hours at room temperature and subsequently the capillary is rinsed with PB7.

Coating of capillaries with antibodies is achieved by filling the capillaries with a mixture of the antibody solution (10 μg protein/ml) and PB7 in case of capillary coupling or by pressure injection for 30 or 60 sec by means of an electropherograph. After injection the capillaries are laid horizontally in order to avoid siphoning of the antibodies through the capillaries during the 3 h incubation at room temperature. Then the capillaries are filled with a solution of BSA in PB7 (1–2 μmg/ml) and incubated for another 3 hours at room temperature in an attempt to reduce non-specific binding.

For the covalent binding of antibodies, a fused silica capillary is first modified with 3-aminopropyltrimethoxysilane function. Glutaraldehyde is used to bind the antibodies to the capillary surface.

Length of antibody coating

The length of the capillary coating preferably equals to the length of the injected plug of antibody solution and can be calculated when the column dimensions, the viscosity of the medium and the applied pressure are known. They also can be estimated by a determination of the relation between the length of the capillary and the break through time of a continuous injection of an aqueous FA solution. Under the assumption that the viscosity of the antibody solution does not differ from that of other aqueous solutions, the injected plug length can be calculated on basis of the injection time.

Coupling of the coated and uncoated capillaries

A 7 cm long coated capillary is coupled to an uncoated fused silica capillary of 30 or 40 cm length, the i.d. of both capillaries is either 50 or 75 μm. By means of a messing holder the capillary can be held in order to polish the capillary ends with a Beckman capillary cutter or with polishing sheets. In that way a zero dead-volume coupling can be obtained. By means of a microscope the surface of the capillary end can be checked. The easiests way to position the capillaries is by using a metal wire with a diameter of 40 or 70 μm for capillaries with an i.d. of 50 or 75 μm, respectively, and push this wire through the 7 cm coated capillary and another 1–2 cm in the fused silica capillary. It is essential that the metal wire is cut by a sharp knife in order to avoid distortion of the end. Bending of the wire should be avoided as well. A glass-fibre plate 10×15×2 mm, normally used as the basis for an electronic print, with a 360 μm deep V-shaped (90 degrees) groove, can be used for the positioning of the capillaries. By means of Katiobond (Delo, Grafelfing, Germany), a UV-polymerising, non-flowing glue, the two capillary ends are glued together after positioning of the connected capillaries in the groove and placing a 250 μm thick deck-glass on top. Then the coupling device is illuminated with an Opticure light gun (Norland, New Brunswick, N.J., USA) for 2–4 min. In order to allow complete polymerisation, it is advisable to wait for 1 hour before using the capillary. After illumination the wire can be withdrawn from the capillaries.

The stability and binding properties of antibodies to the inside wall of the first stage of the capillary system are virtually unaffected by the type of immobilisation and the electrical field across the capillary system. Immobilisation of different antibodies, either mixed in one zone or in separate zones of the first stage of the capillary system provides for the development of combined multianalyte bioaffinity assay and capillary electrophoresis analysis. The advantages of both bioaffinity assay analysis and capillary electrophoresis are used. The claimed invention overcomes the disadvantages of the prior art approaches and provides a device and a method which is readily applicable and results in a high analytical sensitivity.

What is claimed is:

1. A device for combined bioaffinity assay and electrophoretic separation of analyte molecules, which comprises a capillary system having a first capillary channel for performing a bioaffinity interaction between the analyte molecules and molecular recognition elements which am attached to and immobilized on a wall of the first capillary channel and a second capillary channel which is a means for separating the analyte molecules by capillary electrophoresis; and a means for detecting the separated analyte molecules.

2. A device according to claim 1, wherein the capillary system has an internal cross section which is circular, rectangular, trapezoidal or a similar shape.

3. A device according to claim 1, wherein the capillary system has a total length, being the sum of the lengths of the first and the second stage, which amounts to from about 0.1 cm to about 200 cm, preferably to about 1 cm to about 50 cm.

4. A device according to claim 3, wherein the length of the first stage mounts to about 1%–95%, preferably less than 25%, of the total length of the capillary system.

5. A device according to claim 1, wherein the capillary system comprises at least one capillary tube.

6. A device according to claim 5, wherein the capillary system comprises at least two capillary tubes, a first capillary tube being the first stage with molecular recognition elements attached to its inside wall, and a second capillary tube adapted for performing electrophoretic separation and detection of the separated species, which are connected with each other, and are preferably glued together with their end surfaces.

7. A device according to claim 5, wherein the capillary tube(s) is (are) of fused silica and has (have) a cross sectional area of about 5 μm$^2$ to about 100000 μm$^2$.

8. A device according to claim 1, wherein the capillary system is established planarely on a slab of glass, polymer, or semiconducting material by micromachining or by standard techniques used in microelectronic industry.

9. A device according to claim 8, wherein electric couplings for electrodes for establishing an electric field across the capillary system and for detecting signals from a detector for electrophoretically separated species are integrated on the slab of glass or semiconducting material.

10. A device according to claim 8, wherein the first stage of the capillary system is shaped such, that a controlled enlargement of the surface to which the molecular recognition elements are attached, is achieved, while the flow conditions for the analyte molecules remain predictable.

11. A device according to claim 10, wherein the first stage of the capillary system is meander-shaped.

12. A device according to claim 1, wherein the molecular recognition elements are antibodies, or antigens, or receptors, or drugs, or DNA-strands, or carbohydrates, or the like, or mixtures of two or more of those elements.

13. A method for combined bioaffinity and electrophoretic separation, wherein an analyte comprising more than one species of analyte molecules is separated first by bioaffinity and subsequently by electrophoresis by transporting the analyte through a capillary system having two stages, a first capillary stage in which the analyte molecules are captured by molecular recognition elements which are attached to and immobilized on a wall of a first capillary channel and are subsequently dissociated from the molecular recognition elements, and a second stage of the capillary system, in which the analyte-molecules are separated by capillary electrophoresis and subsequently detecting the separated species of analyte-molecules at a terminal part of the capillary system.

14. A method according to claim 13, wherein the analyte molecules are concentrated in the subsequent second stage of the capillary system.

15. A method according to claim 14, wherein the concentration of the analyte molecules is accomplished by Isotachophoresis, or by isoelectrical focussing, or by field amplified sample concentration due to the electrical field in the second stage of the capillary system.

16. A method according to claim 13, wherein as the molecular recognition elements antibodies, or antigenes, or receptors, or drugs, or DNA-strands, or carbohydrates, or the like, or mixtures of two or more of those elements are used.

* * * * *